US009700378B2

(12) United States Patent
Mowlai-Ashtiani (10) Patent No.: US 9,700,378 B2
(45) Date of Patent: Jul. 11, 2017

(54) ENDOSCOPE LENS CLEANING DEVICE (71) Applicant: Medtronic-Xomed, Inc., Jacksonville, FL (US)

(72) Inventor: Ali Mowlai-Ashtiani, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 155 days.

(21) Appl. No.: 13/871,870

(22) Filed: Apr. 26, 2013

(65) Prior Publication Data
US 2014/0318582 A1  Oct. 30, 2014

(51) Int. Cl.
A61B 1/04 (2006.01)
A61B 19/00 (2006.01)
A61B 1/00 (2006.01)
A61B 1/015 (2006.01)
A61B 1/12 (2006.01)
A61B 90/70 (2016.01)

(52) U.S. Cl.
CPC .......... *A61B 19/34* (2013.01); *A61B 1/00135* (2013.01); *A61B 1/015* (2013.01); *A61B 1/126* (2013.01); *A61B 90/70* (2016.02); *A61B 1/00179* (2013.01); *A61B 2090/701* (2016.02)

(58) Field of Classification Search
USPC ................. 600/133, 155–157, 169
See application file for complete search history.

(56) References Cited

U.S. PATENT DOCUMENTS 5,313,934 A * 5/1994 Wiita et al. ............... 600/109
5,400,767 A * 3/1995 Murdoch ................... 600/157
5,464,008 A * 11/1995 Kim ............................... 600/157
5,575,756 A   11/1996 Karasawa et al.
5,637,075 A    6/1997 Kikawada
5,697,888 A * 12/1997 Kobayashi et al. .......... 600/159
6,110,103 A *  8/2000 Donofrio ....................... 600/121

(Continued)

FOREIGN PATENT DOCUMENTS

EP  0664101 A1  7/1995
JP  H06 189893   7/1994

OTHER PUBLICATIONS

International Search Report, PCT/US2014/035488, Aug. 29, 2014, 6 Pages.

*Primary Examiner* — Matthew J Kasztejna
(74) *Attorney, Agent, or Firm* — Dicke, Billig & Czaja, PLLC (57) ABSTRACT An endoscope lens cleaning apparatus used for removing surgical debris from an objective lens of an endoscope. The endoscope lens cleaning apparatus includes an elongated sheath and a connection assembly. The elongated sheath includes an endoscope lumen and an irrigation channel, configured in parallel and adjoining, each extending between an inlet end and an outlet end. At least one stand-off is formed within the elongated sheath along the outlet end. The endoscope lumen and the irrigation channel are fluidly open to one another when the endoscope lumen is in an empty state and the irrigation channel is fluidly sealed from the endoscope lumen between the at least one stand-off and the inlet end when the endoscope lumen is in an occupied state. A fluid passageway extends from a fluid port of the connection assembly and is configured to align and fluidly connected with the irrigation channel.

15 Claims, 9 Drawing Sheets (56) References Cited

U.S. PATENT DOCUMENTS

| | | |
|---|---|---|
| 6,354,992 B1 | 3/2002 | Kato |
| 6,447,446 B1 | 9/2002 | Smith et al. |
| 7,081,097 B2 | 7/2006 | Martone et al. |
| 7,758,497 B2 * | 7/2010 | Hem .................. A61B 1/00094 600/104 |
| 7,811,228 B2 * | 10/2010 | Adams .......................... 600/121 |
| 7,857,784 B2 * | 12/2010 | Schmidberger .... A61B 1/00071 600/115 |
| 8,047,215 B1 * | 11/2011 | Sasaki .......................... 134/95.2 |
| 8,079,952 B2 | 12/2011 | Fujimoto |
| 2009/0247831 A1 | 10/2009 | Miyamoto et al. |
| 2011/0230716 A1 | 9/2011 | Fujimoto |
| 2012/0046524 A1 | 2/2012 | Miyamoto |
| 2012/0101337 A1 | 4/2012 | Clark et al. |
| 2012/0238818 A1 | 9/2012 | O'Prey et al. |

\* cited by examiner

ENDOSCOPE LENS CLEANING DEVICE

BACKGROUND

Endoscopes permit remote viewing of a surgical site while a surgical procedure is being performed. During surgery, blood, tissue or other debris from the surgical site can splatter onto the viewing end of the endoscope, impairing the field of view through the endoscope. The surgical debris obscuring the field view of the endoscope must be removed. Endoscope lenses can be cleaned by providing effective flushing of surgical debris from the distal viewing end of an endoscope.

Endoscope sheaths are used to keep the endoscope insertion body and viewing end of the endoscope clean and often include air tubes, water tubes, or suction tubes to flush away or suction away surgical debris from the viewing end. The irrigation, suction and air tubes on or within the endoscope sheath often add significant girth to the profile of the endoscope. Endoscope sheaths typically are custom fitted to a specific endoscope. Since endoscopes are of different lengths, the sheath is typically required to be a corresponding length.

SUMMARY

One aspect provides an endoscope lens cleaning apparatus used for removing surgical debris from an objective lens of an endoscope. The endoscope lens cleaning apparatus includes an elongated sheath and a connection assembly. The elongated sheath includes an endoscope lumen and an irrigation channel, each extending between an inlet end and an outlet end opposite the inlet end of the elongated sheath. At least one stand-off is formed within the elongated sheath along the outlet end. The irrigation channel is configured parallel and adjoining to the endoscope lumen. The endoscope lumen and the irrigation channel are fluidly open to one another when the endoscope lumen is in an empty state and the irrigation channel is fluidly sealed from the endoscope lumen between the at least one stand-off and the inlet end when the endoscope lumen is in an occupied state. The connection assembly includes a coupling port, an access port, and a fluid port. The coupling port is configured to mate with the inlet end of the elongated sheath. An endoscope passageway extends between the coupling port and the access port and is configured to align with the endoscope lumen of the elongated sheath when mated. A fluid passageway extends from the fluid port and is configured to align and fluidly connected with the irrigation channel.

DETAILED DESCRIPTION

Figure 1:
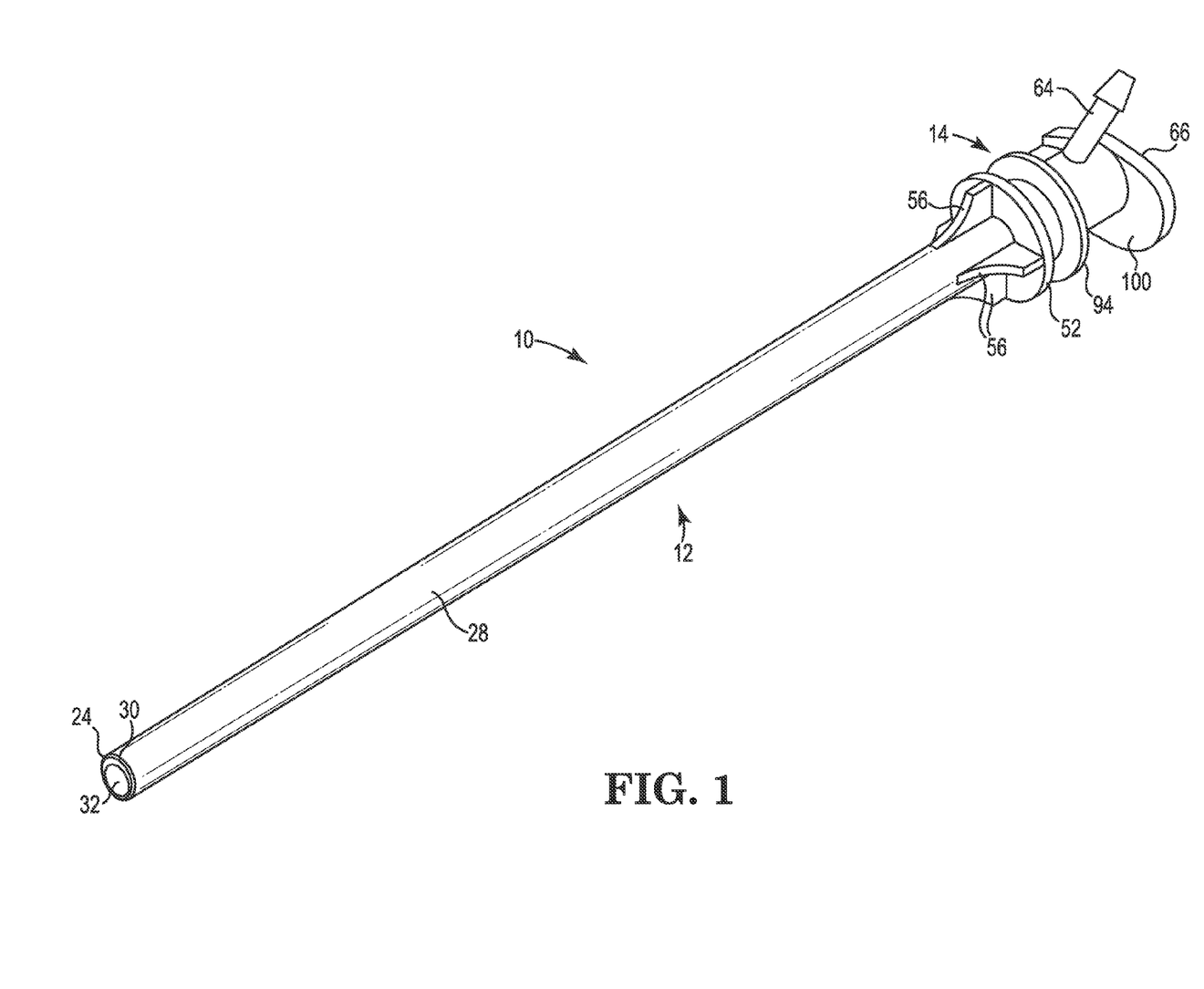
FIG. 1 is a perspective view of an endoscope lens cleaning apparatus in accordance with aspects of the present disclosure.

Some aspects in accordance with the present disclosure relate to an endoscope lens cleaning apparatus for use with an endoscope, fluid supply tubing, pump, and pump controls during an endoscopic procedure. With this in mind, one embodiment of an endoscope lens cleaning apparatus 10 is illustrated in FIG. 1 and includes an elongated sheath 12 and a connection assembly 14. Details on the various components are provided below.

Figure 2:
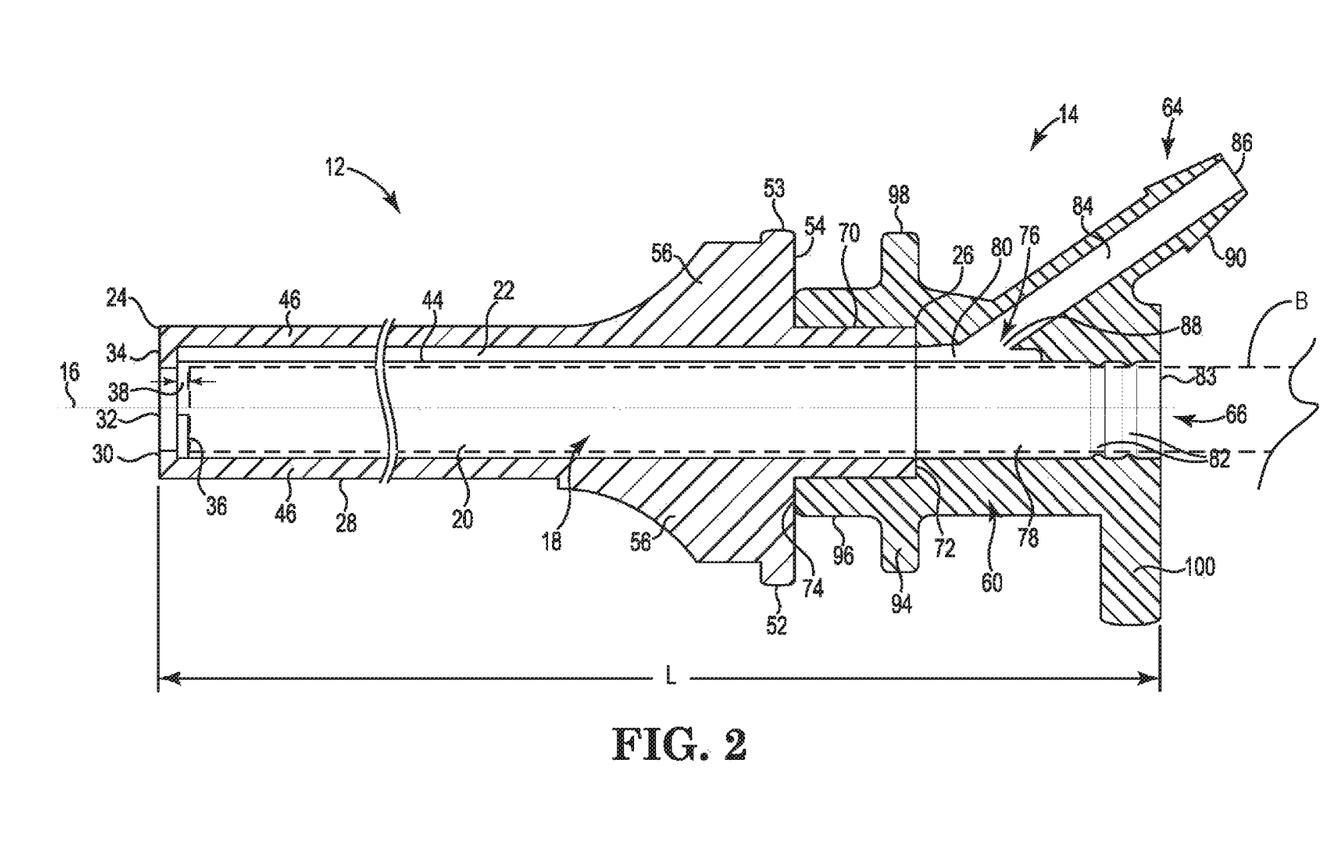
FIG. 2 is a cross-sectional view of an endoscope lens cleaning apparatus of FIG. 1.

In general terms, however, the endoscope lens cleaning apparatus 10, consisting of the elongated sheath 12 and the connection assembly 14, has a length "L", as referenced in FIG. 2. The length "L" that is less than or equal to a total length of an endoscope insertion body. The elongated sheath 12 and the connection assembly 14 are configured for encapsulating at least a partial length of an endoscope insertion body "B" to prevent at least part of the endoscope insertion body "B" from being soiled during the medical procedure. Additionally, the elongated sheath 12 and the connection assembly 14 are configured for delivering fluid (e.g., saline solution) and aspirating some of the fluid back to clean an endoscope lens during an endoscopic procedure. The endoscope lens cleaning apparatus 10 is coupled to a pump (not shown) via fluid supply tubing (not shown) for delivery of a fluid to an endoscope lens and subsequent removal of the fluid and surgical debris by suctioning.

The elongated sheath 12 includes or defines a conduit 18 including an endoscope lumen 20 and an irrigation channel 22. The endoscope lumen 20 and the irrigation channel 22 are adjoined to be fluidly open to one another, and extend parallel to one another, from an outlet end 24 to an opposing inlet end 26 of the elongated sheath 12. The elongated sheath 12 is configured to accommodate an endoscope lumen 20 that is larger than the irrigation channel 22 and minimize an outer size of the elongated sheath 12. In one embodiment, as best shown in FIG. 3B, an outer surface 28 of the elongated sheath 12 is asymmetrical, having a greater depth "D" than width "W". Other shapes of the elongated sheath 12, such as cylindrical, are also acceptable.

The elongated sheath 12 terminates at the outlet end 24 having an inwardly projecting transverse radial flange 30 defining a distal opening 32 suitable for endoscope lens viewing. An extended flange portion 34 of the flange 30 projects across at least a portion of the irrigation channel 22 at the outlet end 24 to direct flow across the endoscope lens (not shown) and the distal opening 34. At least one stand-off 36 is disposed adjacent the flange 30 within the conduit 18 and is configured to space the endoscope viewing end carrying the objective lens away from the flange 30 a predetermined distance when the endoscope is fully inserted (endoscope not shown). The at least one stand-off 36 can be radially spaced bumps with rounded edges, rectangular sections, or any shape suitable to keep the endoscope viewing end from being positioned directly against the flange 30 when fully inserted into the endoscope lumen 20. The size and shape of the at least one stand-off 36 is appropriate to accommodate the desired flow across the endoscope lens when flushing and debris removal when suctioning. The at least one stand-off 36 provides a distal gap 38 for fluid to flow out of the irrigation channel 22 at the outlet end 24 between the extended flange 34 and the endoscope viewing end. The distal gap 38 is sized such that irrigating solution directed into the irrigation channel 22 is redirected by the extended flange 34 in order to flow across the endoscope lens and flush surgical debris from the viewing end of the endoscope.

Figure 3A:
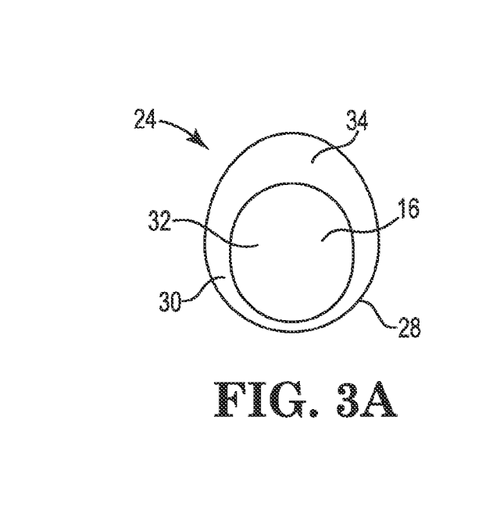
FIG. 3A is an outlet end view of an elongated sheath of the apparatus of FIG. 1.
Figure 3B:
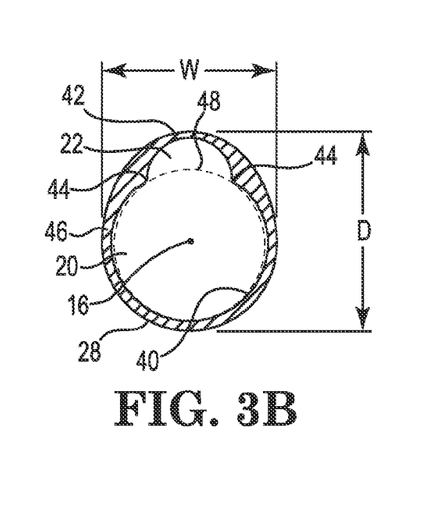
FIG. 3B is a cross-sectional view of the elongated sheath of the apparatus of FIG. 1.

As best illustrated in FIGS. 3A and 3B, the conduit 18 is defined in cross-section by intersecting cylindrical lumens, or passageways, consisting of the endoscope lumen 20 and the irrigation channel 22. A cross-sectional view of the conduit 18 can appear similarly shaped to an outer perimeter of a figure "8", without any division between a top and a bottom portion of the figure "8". In other words, the irrigation channel 22 is offset from the endoscope lumen along the endoscope path axis 16. The endoscope lumen 20 can be larger (e.g., has a larger diameter) and occupies a greater volume of the elongated sheath 12 than the irrigation channel 22. The endoscope lumen 20 and the irrigation channel 22 are fluidly open to one another when the endoscope lumen 20 is in an empty or unoccupied state (i.e., not occupied by an endoscope) and fluidly closed and sealed from one another, between the at least one stand-off 36 and the inlet end 26, when the endoscope lumen 20 is in an occupied state (i.e., occupied by an endoscope having an outside diameter sufficient to seal against the main body inner surface 40).

A main body inner surface 40 partially defines the endoscope lumen 20 and an irrigation inner surface 42 partially defines the irrigation channel 22. The main body inner surface 40 and irrigation inner surface 42 intersect along the conduit 18 parallel to an endoscope path axis 16 at junctions 44 extending from the inlet end 26 to the outlet end 24. In one embodiment, the irrigation inner surface 42 is semi-circular in cross-section and the main body inner surface 40 is formed as an incomplete circle adjoining the semi-circular irrigation inner surface 42 along the junctions 44. The irrigation inner surface 42 has a radius that is smaller than a radius of the main body inner surface 40. The surfaces 40, 42 diverge from the outer surface 28 to create varying thicknesses of the perimeter wall 46. The perimeter wall 46 can range from 0.001 to 0.015 inches thick, for example. The outer surface 28 provides a smooth surface for insertion into the patient's body.

Figure 3C:
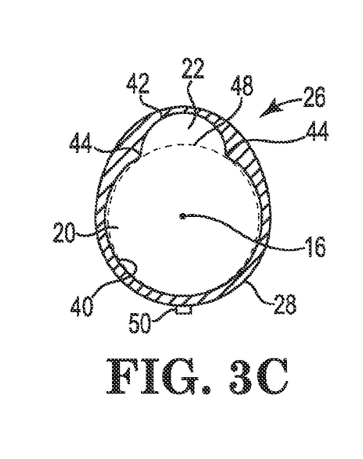
FIG. 3C is an inlet end view of the elongated sheath of the apparatus of FIG. 1.

As indicated by a dashed curved line 48 generally indicating an outside perimeter of the endoscope in FIGS. 3B and 3C, the irrigation channel 22 extends directly along an outside surface of the endoscope positioned within the endoscope lumen 20. In other words, an outside surface of the endoscope exposed to the irrigation channel 22 separates the endoscope lumen 20 from the irrigation channel 22 and fully encloses the irrigation channel 22 (up to the at least one stand-off 36 adjacent to the flange 30, not shown) when inserted. The endoscope lumen 20 is sized to provide a fluid-tight seal against the endoscope with respect to the irrigation channel 22 along the junctions 44. Radii of the junctions 44 form a seal against the perimeter of the endoscope. The main body inner surface 40 is relatively smooth and allows the endoscope to be inserted with minimal frictional resistance. The elongated sheath 12 can be flexible to allow unrestricted bending of a flexible portion of the insertion body or may be relatively rigid.

FIG. 3C is a cross-section of the inlet end 26 of the elongated sheath 12. The inlet end 26 of the elongated sheath 12 is open. With continued reference to FIG. 2, in one embodiment, the inlet end 26 includes an alignment mechanism 50 for aligning the elongated sheath 12 with the connection assembly 14 along the endoscope path axis 16. In one embodiment, the alignment mechanism 50 is a key which projects outwardly from the outer surface 28 of the elongated sheath 12 and mateably couples to a slot 68 of the connection assembly, described further below. In one embodiment, the elongated sheath 12 and the connection assembly 14 are fixedly coupled together by adhesive or other attachment means. The elongated sheath 12 and the connection assembly 14 can be polypropylene or other suitable material and can be translucent, if desired.

Returning to FIGS. 2 and 3A, the outlet end 24 of the elongated sheath 12 has a zero degree angled end for use with zero degree angled endoscopes. A zero degree angle outlet end 24 includes the flange 30 and extended flange 34 disposed perpendicular to the endoscope path axis 16 and the perimeter walls 46 of the elongated sheath 12.

Examples of alternative embodiments to the zero degree angled outlet end 24 of FIG. 2 are illustrated in FIGS. 4A-4B and 5A-5B. In general, endoscopes are manufactured with objective lenses disposed at angles ranging from 0 degrees to 70 degrees with respect to a longitudinal axis of the endoscope. Accordingly, endoscope sheaths 12, 12', 12" of the present disclosure include outlet ends 24, 24', 24" are configured for use with various angled endoscopes. In accordance with aspects of the present disclosure, the outlet ends 24, 24', 24" are configured to accommodate endoscope viewing ends of various manufacturers, including those that have rounded or squared edged viewing ends, for example.

Figure 4A:
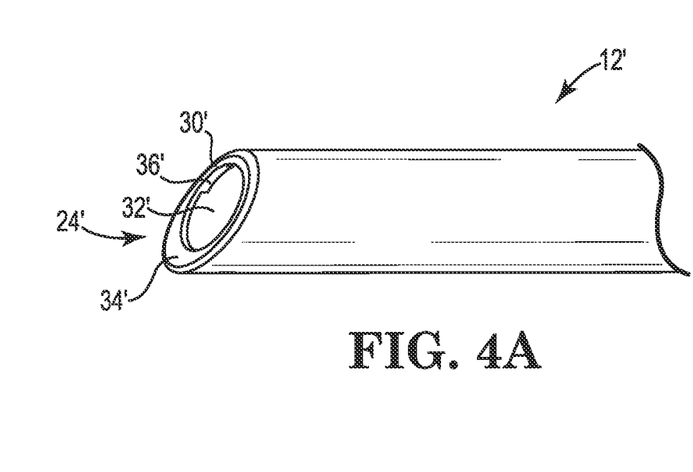
FIG. 4A is a perspective view of an angled outlet end of an elongated sheath in accordance with aspects of the present disclosure.
Figure 4B:
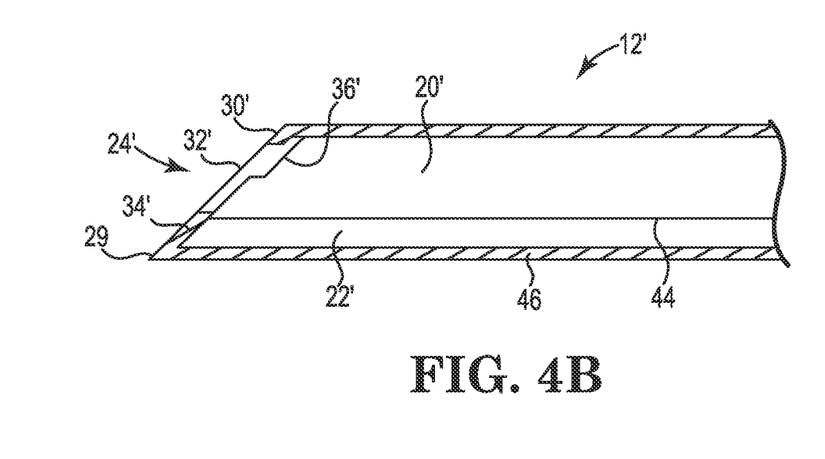
FIG. 4B is a cross-sectional view the angled outlet end of the elongated sheath of FIG. 4A.

With further reference example embodiment illustrated in FIGS. 4A and 4B, the outlet end 24' forms a plane that is angled with respect to the endoscope path axis 16. The embodiment illustrated in FIGS. 4A and 4B can be used with a 45 degree or 30 degree angled endoscope, for example. In this configuration, outlet end 24' projects farthest along the irrigation channel 22', terminating at a tip 29, and tapers back along the endoscope lumen 20'. In this regard, an extended flange 34' and a flange radially project toward a distal opening 32' along the angled plane of the outlet end 24' to direct an irrigation flow along the distal opening 32' and endoscope lens. At least one stand-off 36' is disposed within the endoscope lumen 20' along the flange 30' and is sized to define and maintain a predetermined irrigation space between the outlet end 24' of the elongated sheath 12' and the angled endoscope lens. Similar to other embodiments, the at least one stand-off 36' is configured to position the endoscope viewing end inside the elongated sheath 12' relative to the outlet end 24'.

Figure 5A:
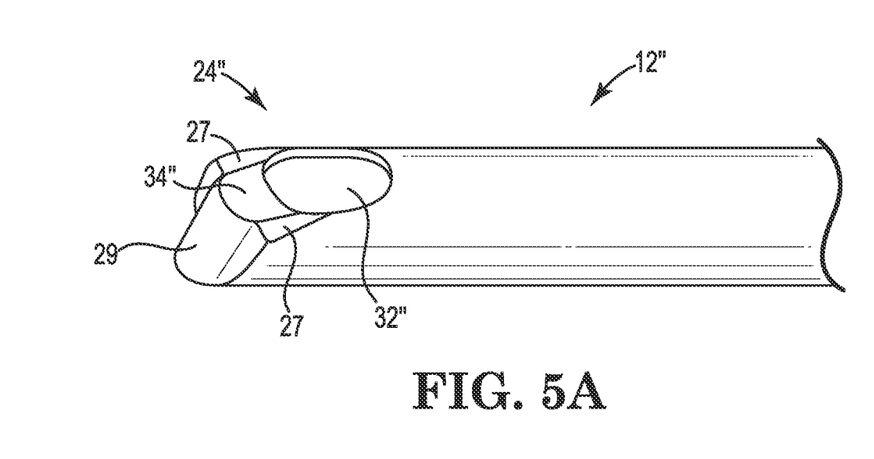
FIG. 5A is a perspective view of an angled outlet end of an elongated sheath in accordance with aspects of the present disclosure.
Figure 5B:
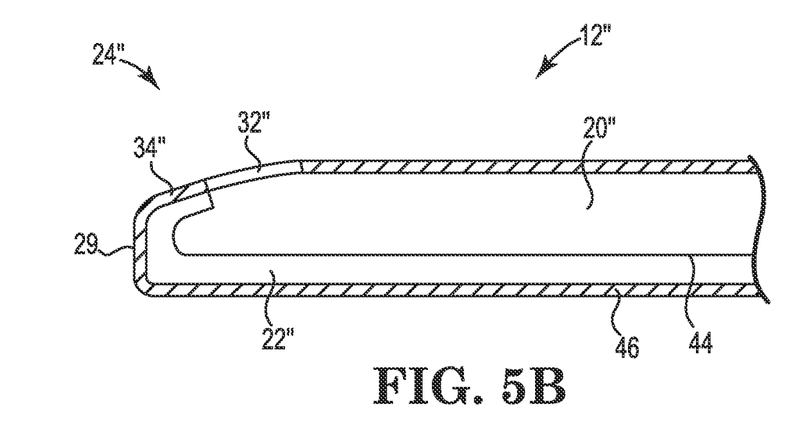
FIG. 5B is a cross-sectional view the angled outlet end of the elongated sheath of FIG. 5A.

An elongated sheath 12" including an outlet end 24" illustrated in FIGS. 5A and 5B is configured to accommodate endoscopes having 70 degree angled endoscope viewing ends. Again, similar to other embodiments, with the endoscope viewing end positionable inside the elongated sheath 12" relative to the outlet end 24", various configurations of manufactured 70 degree angled endoscope viewing ends can be used with elongated sheath 12". A relationship of an irrigation channel 22" and a distal opening 32" is illustrated in FIG. 5B. As shown, the irrigation channel 22" extends along a perimeter wall 46 and is redirected by an end wall 29 and redirected again by an extended flange 34" toward the distal opening 32". Insets 27 are configured to position the endoscope viewing end inside the elongated sheath relative to the outlet end 24".

Figure 6A:
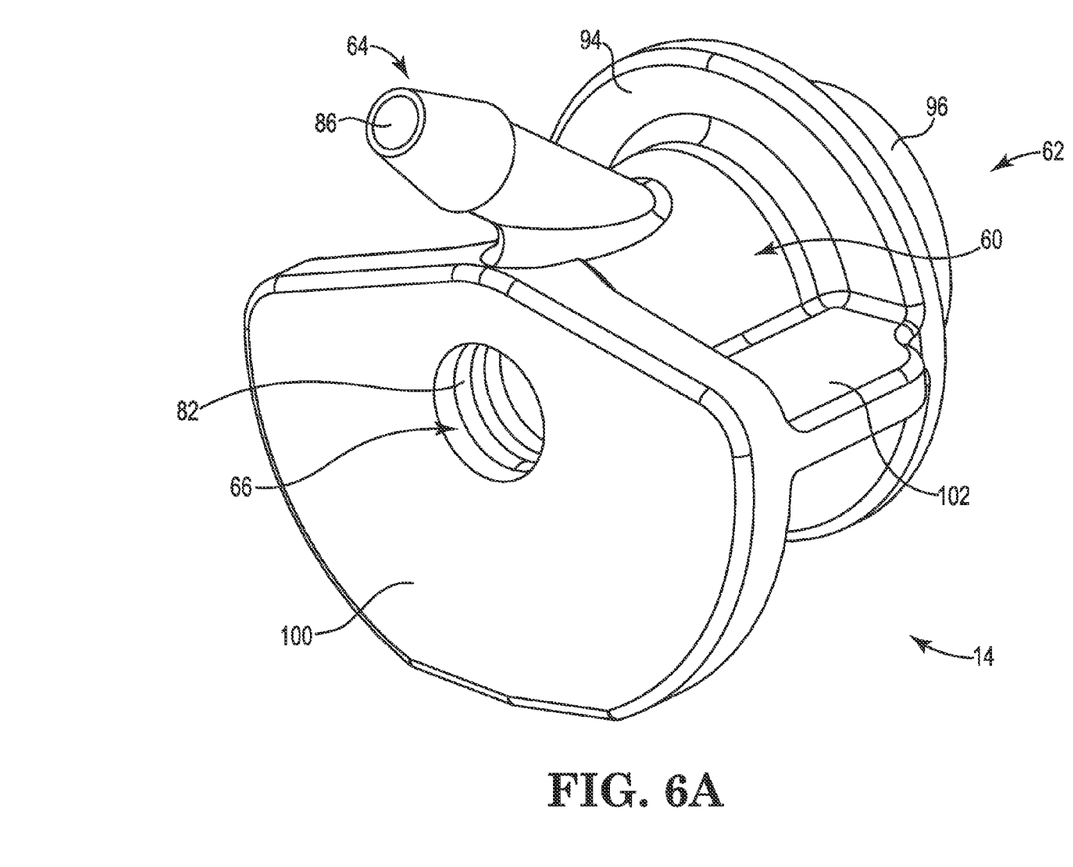
FIGS. 6A-6B are perspective views of a connection assembly of the apparatus of FIG. 1.
Figure 6B:
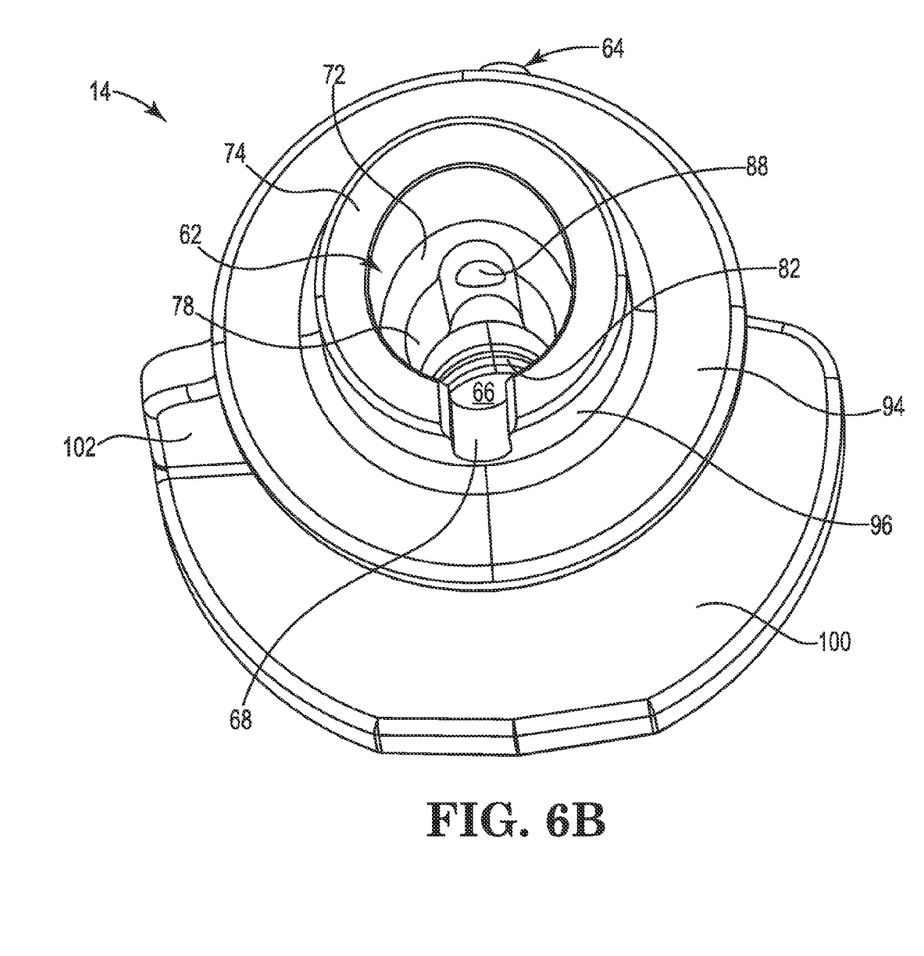

With reference to FIGS. 6A and 6B, the connection assembly 14 includes a manifold housing 60 forming or providing a coupling port 62, a fluid port 64, and an access port 66 which are described more fully below. As best shown in FIG. 2, the housing 60 fluidly interconnects the ports 62-66. The access port 66 is configured to allow insertion of an endoscope into the housing 60, and in particular through the coupling port 62. Thus, in some embodiments, the access port 66 is axially aligned with the coupling port 62. The coupling port 62 is best illustrated in FIGS. 1 and 6B and is configured for fluid connection to the inlet 26 of the elongated sheath 12. The coupling port 62 can include a slot 68 configured to mate with the alignment mechanism 50 useful in establishing and maintaining the desired alignment and connection of the elongated sheath 12 to the connection assembly 14.

The coupling port 62 may be removably coupled or fixedly coupled to the inlet 26. The coupling port 62 is sized and shaped to correspondingly mate with the inlet 26. Accordingly, if the outer surface of the inlet 26 is asymmetrical or oblong in cross-section, then a mating surface 70 of the coupling port is asymmetrical or oblong in cross-section. With this configuration, the inlet 26 is insertable into the coupling port 62. In one embodiment, the coupling port 62 includes an abutment 72 against which the inlet 26 terminates when fully inserted. In addition, the inlet 26 can extend within the coupling port 62 such that a terminal end 74 of the coupling port 62 abuts the face 54 of the radial shoulder 52.

An irrigation passageway 76 and an endoscope passageway 78 are established within the housing 60. In particular, the irrigation passageway 76 extends through the coupling port 62 and the fluid port 64. The irrigation passageway 76 includes a channel portion 80 that corresponds in shape and size to, and is axially aligned with, the irrigation channel 22 of the elongated sheath 12. The fluid port 64 projects at an obtuse angle relative to the coupling port 62. The fluid port 64 forms a lumen 84 extends between a fluid inlet 86 and a fluid outlet 88. The fluid port 64 is open relative to the channel portion 80. The lumen 84 and the channel portion 80 form the irrigation passageway 76. The fluid port 64 can include various features at fluid inlet 86 that promote fluid connection to tubing or other components associated with a source of fluid useful in for cleaning (or "flushing" and "suctioning") the endoscope lens when inserted within the endoscope lens cleaning apparatus 10. For example, a barbed surface 90 is optionally formed. The fluid port 64 corresponds with a dimensional attribute of the tubing (not shown) to better ensure that the fluid introduced at the fluid port 64 interfaces with the endoscope lens inserted at the outlet 24 of the elongated sheath 12. The fluid port 64 extends a predetermined distance relative to the access port 66 for ease of connection the tubing or other components.

The endoscope passageway 78 extends through the coupling port 62 and the access port 66. The channel portion 80 of the irrigation passageway 76 extends parallel to the endoscope passageway 78 through the housing 60 and terminates distal to, or interior of, circumferential ridges 82 positioned within the access port 66. Circumferential ridges 82 project inwardly along the endoscope passageway 78 and fit against an outside diameter of the endoscope insertion body to provide a fluid-tight, frictional seal against the endoscope insertion body extending through an endoscope inlet 83 of the access port 66. The endoscope inlet 83 and the endoscope lumen 20 can have the same diameter. The endoscope passageway 78 corresponds in shape and size to, and is axially aligned with, the endoscope lumen 20 of the elongated sheath 12. The complimentary shapes of the coupling port 62 and the inlet 26 along with the alignment mechanism 50 and the slot 68, when applicable, are used to assist aligning the irrigation channel 22 with the irrigation passageway 76 and the endoscope channel 20 with the endoscope passageway 78.

Figure 7:
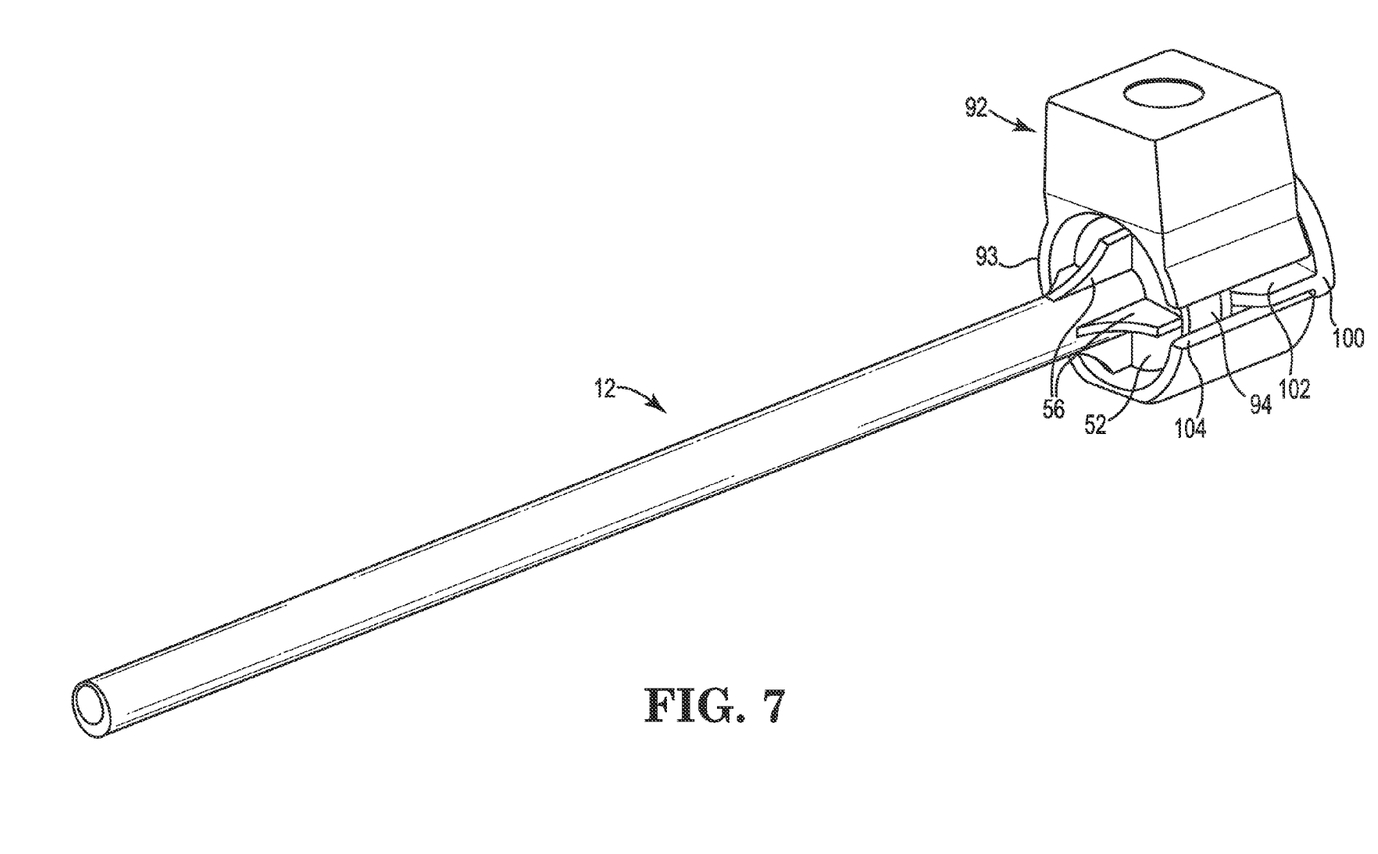
FIG. 7 is a perspective view of an endoscope lens cleaning apparatus in accordance with aspects of the present disclosure coupled with a control switch housing.

As indicated above, the endoscope lens cleaning apparatus 10 is configured for use with a pump for supply and removing fluid. With this in mind, one construction of the connection assembly 14 includes the housing 60 configured to accommodate attachment of a control switch housing 92. The control switch housing 92 is shown in FIG. 7 for illustrative purposes only and can be any available control switch housing. Details of the housing 60 of the connection assembly 14 configured to accept the control switch housing 92 are provided below. In general terms, however, the housing 60 includes a radial hub 94, a nose 96, an end plate 100, and an interceptor 10.

One construction of the housing 60, in accordance with the present disclosure, is shown in greater detail in FIGS. 6A and 6B. The radial hub 94 extends transverse the endoscope path axis 16 and the nose 96 extends between the terminal end 74 of the coupling port 62 and the radial hub 94. In one embodiment, a perimeter edge 98 of the radial hub 94 and a perimeter edge 53 of the radial shoulder 52 extend transverse the endoscope path axis 16 equally. The perimeter edges 53, 98 can be circular, asymmetrical or any desired shape consistent with accommodating the coupling and support of the control switch housing 92. Similar to the radial hub 94, the end plate 100 extends transverse to the endoscope path axis 16. However, the end plate 100 is not circular and is configured such that it does not extend toward, and interfere with, the fluid port 64. The end plate 100 can provide a convenient location for a user to hold onto the connection assembly 14. The interceptor 102 extends linearly between the radial hub 94 and the end plate 100 along one side of the housing 60.

The control switch housing 92 includes a partially cylindrical wall segment 93 sized to receive and be releasably mounted onto the endoscope lens cleaning apparatus 10. When the control switch housing 92 is mounted to the endoscope lens cleaning apparatus 10, as illustrated in FIG. 7, the wall segment 93 of the control switch housing 92 generally encircles the radial shoulder 52 of the elongated sheath 12 and the radial hub 94 of the connection assembly 14 and abuts the end plate 100. Further, the interceptor 102 is configured to extend between terminating edges 104 of the control switch housing 92. The interceptor 102 prevents the control switch housing from 92 rotating about the endoscope lens cleaning apparatus 10.

Figure 8:
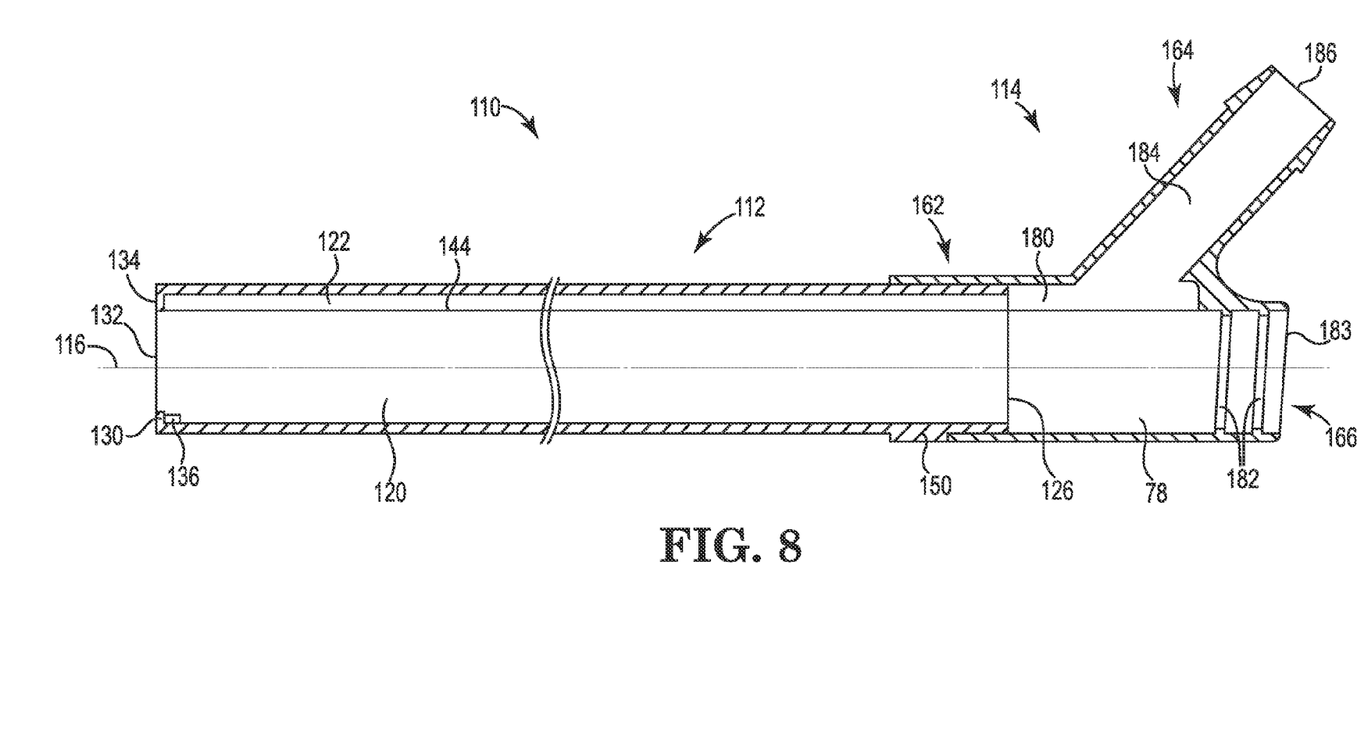
FIG. 8 is a cross-sectional view of an endoscope lens cleaning apparatus in accordance with aspects of the present disclosure.

FIG. 8 illustrates a perspective view of an endoscope lens cleaning apparatus 110 according to one embodiment. Aspects of the endoscope lens cleaning apparatus 110 are similar to those discussed above and similar elements are correspondingly numbered. In this embodiment, an inlet end 126 of an elongated sheath 112 is inserted into a coupling port 162 of a coupling assembly 114. An alignment mechanism 150 can be included to properly align an irrigation channel 122 and an endoscope lumen 120 of the elongated sheath 112 with the irrigation passageway 176 and endoscope passageway 178 of the connection assembly 114, respectively.

Similar to previous embodiments, the connection assembly 114 includes the coupling port 162, a fluid port 164, and an access port 166. Exteriors of the ports 162-166 are generally cylindrical. The coupling port 162 and access port 166 are axially aligned to permit an endoscope to extend along an endoscope path axis 116 extending through the access port 166, the coupling port 162 and the elongated sheath 112. The connection assembly 114 can include a "winged" extension (not shown), similar to end plate 100 of the previous embodiments, to allow for convenient gripping by a user during insertion and removal of the endoscope insertion body and also for positioning the endoscope and endoscope lens cleaning apparatus 110 within a patient.

As described above, and with general reference to the embodiment of FIGS. 1 and 2, a method of endoscope lens cleaning in accordance with the present disclosure includes inserting the endoscope insertion body into the coupling assembly 14 and the elongated sheath 12 of the endoscope lens cleaning apparatus 10. Since the length "L" of the endoscope lens cleaning apparatus 10 can be less than a length of the endoscope insertion body, a first portion of the endoscope insertion body can be disposed within the endoscope lens cleaning apparatus and a second portion can be disposed distal to the endoscope lens cleaning apparatus. The irrigation channel 22, extending proximal to the at least one stand-off 36, and irrigation passageway 76 are fluidly sealed from the endoscope lumen 20 and endoscope passageway 78 by the outer surface of the endoscope insertion body. A fluid flow is established through the irrigation channel 22 and irrigation passageway 76 directly along the outer surface to the outlet end 24 of the elongated sheath 12. The fluid is introduced across the endoscope by redirecting the fluid along the extended flange 34. The endoscope lens is spaced a predetermined distance from the flange 30, 34 to allow the fluid to exit the irrigation channel 22. The fluid and surgical debris can further be suctioned, or aspirated, from the endoscope lens and back through the irrigation channel 22 and passageway 76 by reversing the action of the pump connected to the fluid port 64. In accordance with the present disclosure, a single fluid path within the apparatus 10, comprising the irrigation channel 22 and irrigation passageway 76, is used to supply and aspirate fluid.

Although the present disclosure has been described with reference to preferred embodiments, workers skilled in the art will recognize that changes can be made in form and detail without departing from the spirit and scope of the present disclosure.

What is claimed is:

1. An endoscope lens cleaning apparatus for removing surgical debris from an objective lens of an endoscope, comprising:
   an elongated sheath including an endoscope lumen and an irrigation channel, each extending between an inlet end and an outlet end opposite the inlet end of the elongated sheath, wherein the outlet end defines a distal end of the endoscope lens cleaning apparatus, wherein at least one stand-off is formed within the elongated sheath along the outlet end, wherein the irrigation channel is configured parallel and adjoining to the endoscope lumen, wherein the irrigation channel is non-coaxial to the endoscope lumen, wherein the endoscope lumen and the irrigation channel are fluidly open to one another when the endoscope lumen is in an empty state, and wherein the irrigation channel is fluidly sealed from the endoscope lumen between the at least one stand-off and the inlet end when the endoscope lumen is in an occupied state; and
   a connection assembly including a manifold housing forming a coupling port, an access port, and a fluid port, wherein the coupling port is configured to mate with the inlet end of the elongated sheath, and wherein the access port defines a proximal end of the endoscope lens cleaning apparatus, wherein an interior surface of the access port includes circumferential ridges configured to fluidly and frictionally seal against an endoscope insertion body of the endoscope;
   wherein an endoscope passageway extends between the coupling port and the access port and is configured to matingly axially align with the endoscope lumen of the elongated sheath when mated,
   wherein the endoscope passageway and endoscope lumen have a substantially equivalent diameter between the distal and proximal ends of the endoscope lens cleaning apparatus,
   wherein the proximal end is configured to terminate along the endoscope insertion body of the endoscope independent of a non-insertion portion of the endoscope,
   wherein a fluid passageway extends from the fluid port and includes a channel portion that is configured to matingly axially align and fluidly connect with the irrigation channel, and
   wherein the endoscope passageway and the fluid passageway are fluidly open to one another in the empty state and fluidly sealed from one another in the occupied state.

2. The apparatus of claim 1, wherein a radius of the irrigation channel is smaller than a radius of the endoscope lumen.

3. The apparatus of claim 1, wherein the outlet end includes an inwardly projecting transverse radial flange defining a distal opening.

4. The apparatus of claim 3, wherein an extended flange portion of the flange projects across at least a portion of the irrigation channel at the outlet end and is configured to direct flow across the endoscope lens.

5. The apparatus of claim 3, wherein the at least one stand-off is disposed adjacent to the flange within the elongated sheath.

6. The apparatus of claim 1, wherein the access port is sized and configured to provide a fluid tight seal against an endoscope insertion body of the endoscope.

7. The apparatus of claim 1, wherein an interior surface of a conduit extending within the elongated sheath is defined by the endoscope lumen adjoined to the irrigation channel.

8. The apparatus of claim 1, wherein an outer surface of the elongated sheath is asymmetrical.

9. An endoscope lens cleaning apparatus for removing surgical debris from an objective lens of an endoscope, comprising:
   an elongated sheath having an interior surface and an exterior surface, the interior surface diverging from the exterior surface and defined by an irrigation channel adjoined and fluidly open to an endoscope lumen extending between an outlet end and an inlet end, the outlet end includes an inwardly projecting transverse radial flange defining a distal opening and at least one stand-off in the endoscope lumen proximal to the flange, wherein the irrigation channel is parallel and axially offset from a longitudinal axis of the endoscope path; and
   a connection assembly including a manifold housing forming a coupling port, an access port, and a fluid port, wherein the coupling port is configured to mate with the inlet end of the elongated sheath, wherein the inlet end is insertable into the coupling port, wherein the access port has a terminal end opposite the coupling port, wherein a fluid passageway extends between the fluid port and the irrigation channel of the elongated sheath and an endoscope passageway extends between the endoscope lumen and the terminal end of the access port when the connection assembly is mated with the elongated sheath, wherein a proximal end of the connection assembly is configured to terminate along an endoscope insertion body of an endoscope, wherein an interior surface of the access port includes circumferential ridges configured to fluidly and frictionally seal against the endoscope insertion body, and wherein the terminal end includes an end plate extending transverse to the longitudinal axis and configured for a user's hand to grasp.

10. The apparatus of claim 9, wherein the connection assembly is configured to accommodate mounting of a pump control switch housing.

11. The apparatus of claim 9, wherein an irrigation inner surface of the irrigation channel is adjoined to a main body inner surface of the endoscope lumen at junctions extending between the outlet end and the inlet end.

12. The apparatus of claim 9, wherein an endoscope inlet formed at the access port and the endoscope lumen are substantially the same diameter.

13. The apparatus of claim 9, wherein the elongated sheath has a greater cross-sectional depth than width.

14. The apparatus of claim 9, wherein the elongated sheath includes an alignment key and the connection assembly includes a slot configured to accommodate the alignment key.

15. The apparatus of claim 9, wherein the inwardly projecting transverse radial flange includes an extended flange portion along the irrigation channel.

* * * * *